(12) United States Patent
Kamata et al.

(10) Patent No.: US 10,634,896 B2
(45) Date of Patent: *Apr. 28, 2020

(54) MEDICAL OBSERVATION APPARATUS AND MEDICAL OBSERVATION SYSTEM THAT CONVERT AN IMAGING SIGNAL TO AN OPTICAL SIGNAL

(71) Applicant: SONY OLYMPUS MEDICAL SOLUTIONS INC., Tokyo (JP)

(72) Inventors: Yoshiyuki Kamata, Tokyo (JP); Kenji Hirose, Tokyo (JP); Shigeru Tamura, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,867

(22) Filed: Aug. 23, 2018

(65) Prior Publication Data

US 2018/0364471 A1 Dec. 20, 2018

Related U.S. Application Data

(63) Continuation of application No. 15/501,216, filed as application No. PCT/JP2015/074897 on Sep. 1, 2015, now Pat. No. 10,114,208.

(30) Foreign Application Priority Data

Sep. 16, 2014 (JP) .................................. 2014-188108

(51) Int. Cl.
*G02B 21/18* (2006.01)
*G02B 21/36* (2006.01)
(Continued)

(52) U.S. Cl.
CPC ............ *G02B 21/362* (2013.01); *A61B 90/20* (2016.02); *A61B 90/25* (2016.02); *G02B 7/001* (2013.01);
(Continued)

(58) Field of Classification Search
CPC ......................... G02B 21/362; G02B 21/0012; G02B 21/006; G02B 21/008; G02B 21/241;
(Continued)

(56) References Cited

U.S. PATENT DOCUMENTS 3,762,796 A 10/1973 Heller
3,776,614 A 12/1973 Kloots
(Continued)

FOREIGN PATENT DOCUMENTS

CN 101579260 A 11/2009
JP 7-227398 A 8/1995
(Continued)

OTHER PUBLICATIONS

International Search Report dated Dec. 1, 2015, in PCT/JP2015/074897, filed Sep. 1, 2015.
(Continued)

*Primary Examiner* — Arnel C Lavarias
(74) *Attorney, Agent, or Firm* — Xsensus LLP

(57) ABSTRACT

A medical observation apparatus includes a columnar microscope unit configured to image a minute part of an object to be observed with magnification and thereby output an imaging signal. A support unit includes a first joint unit holding the microscope unit in a rotationally movable manner around a first axis parallel to a height direction of the microscope unit, a first arm unit holding the first joint unit and extending in a direction different from the height direction of the microscope unit, a second joint unit holding the first arm unit in a rotationally movable manner around a (Continued)

second axis orthogonal to the first axis, and a second arm unit holding the second joint unit. In a plane passing through the first and second axes, a cross section of the microscope unit, the first and second joint units, and the first and second arm units is included in a circle that has a center at a focus position of the microscope unit and passes through an end point of the first joint unit that is at the maximum distance from the focus position.

19 Claims, 10 Drawing Sheets

(51) Int. Cl.
    *G02B 21/00*     (2006.01)
    *G02B 21/24*     (2006.01)
    *G02B 7/00*     (2006.01)
    *A61B 90/20*     (2016.01)
    *A61B 90/25*     (2016.01)
    *A61B 90/00*     (2016.01)

(52) U.S. Cl.
    CPC ......... *G02B 21/006* (2013.01); *G02B 21/008* (2013.01); *G02B 21/0012* (2013.01); *G02B 21/24* (2013.01); *G02B 21/241* (2013.01); *G02B 21/248* (2013.01); *G02B 21/361* (2013.01); *A61B 90/361* (2016.02)

(58) Field of Classification Search
    CPC .... G02B 21/248; G02B 21/361; G02B 21/00; G02B 21/0004; G02B 21/012; G02B 21/002; G02B 21/0028; G02B 21/0052; G02B 21/0076; G02B 21/06; G02B 21/18; G02B 21/20; G02B 21/22; G02B 21/24; G02B 21/26; G02B 21/36; G02B 21/364; G02B 21/368
    USPC ....... 359/368, 362, 363, 369, 372, 384, 385, 359/391; 600/160, 182; 250/200, 201.1, 250/201.2, 201.3
    See application file for complete search history.

(56) References Cited

U.S. PATENT DOCUMENTS

| | | | |
|---|---|---|---|
| 5,288,043 A | 2/1994 | Tigliev | |
| 5,667,186 A | 9/1997 | Luber et al. | |
| 6,434,416 B1 | 8/2002 | Mizoguchi | |
| 6,493,134 B2* | 12/2002 | Pensel | G02B 21/0012 |
| | | | 359/368 |
| 8,038,108 B2 | 10/2011 | Yasunaga | |
| 9,861,266 B2* | 1/2018 | Kinouchi | A61B 1/04 |
| 10,085,803 B2* | 10/2018 | Higuchi | A61B 90/50 |
| 10,114,208 B2* | 10/2018 | Kamata | G02B 21/24 |
| 10,271,921 B2* | 4/2019 | Kobayashi | G02B 21/32 |
| 10,405,733 B2* | 9/2019 | Michihata | A61B 1/07 |
| 2005/0228257 A1 | 10/2005 | Ishikawa et al. | |
| 2007/0188603 A1 | 8/2007 | Riederer | |
| 2009/0190209 A1 | 7/2009 | Nakamura | |
| 2009/0283647 A1 | 11/2009 | Yasunaga et al. | |
| 2011/0128438 A1* | 6/2011 | Yamashita | G06T 1/00 |
| | | | 348/384.1 |
| 2016/0367134 A1* | 12/2016 | Su | A61B 3/102 |
| 2017/0245743 A1* | 8/2017 | Miyahara | A61B 1/00117 |
| 2018/0168767 A1* | 6/2018 | Hirose | A61B 90/25 |
| 2018/0200017 A1* | 7/2018 | Kobayashi | G02B 21/32 |
| 2018/0235721 A1* | 8/2018 | Tamura | G02B 21/24 |

FOREIGN PATENT DOCUMENTS

| | | |
|---|---|---|
| JP | 08-197482 | 8/1996 |
| JP | 8-197482 A | 8/1996 |
| JP | 2002-272760 A | 9/2002 |
| JP | 2004-117596 A | 4/2004 |
| JP | 2005-43458 A | 2/2005 |
| JP | 2005-87249 A | 4/2005 |
| JP | 2005-224367 A | 8/2005 |
| JP | 2005-292320 A | 10/2005 |
| JP | 2006-305156 | 11/2006 |
| JP | 2006-305156 A | 11/2006 |
| JP | 2013-97031 A | 5/2013 |
| WO | WO 2012/014944 | 2/2012 |
| WO | WO2012/014944 A1 | 2/2012 |

OTHER PUBLICATIONS

Extended European Search Report for corresponding EP 15842643, dated Mar. 16, 2018, 7pgs.
Office Action dated Jun. 12, 2018 in corresponding Japanese Patent Application No. 2014-188108, 11 pages.
Office Action dated Aug. 28, 2018 in corresponding Japanese Patent Application No. 2014-188108, 9 pages.
Combined Chinese Office Action and Search Report dated Dec. 11, 2018 in Chinese Patent Application No. 2015800481593 (with English translation), 20 pages.

* cited by examiner

MEDICAL OBSERVATION APPARATUS AND MEDICAL OBSERVATION SYSTEM THAT CONVERT AN IMAGING SIGNAL TO AN OPTICAL SIGNAL

CROSS-REFERENCE TO RELATED APPLICATIONS

The present application is a continuation of and claims the benefit of priority under 35 U.S.C. § 120 to U.S. application Ser. No. 15/501,216, filed Feb. 2, 2017, the entire contents of which is hereby incorporated herein by reference, and which is a national stage of International Application No. PCT/JP2015/074897, filed Sep. 1, 2015, which claims the benefit of priority under 35 U.S.C. § 119 to Japanese Patent Application No. 2014-188108, filed Sep. 16, 2014.

TECHNICAL FIELD

The present disclosure relates to a medical observation apparatus and a medical observation system with which a minute part of an object to be observed is observed.

BACKGROUND ART

Thus far, as a medical observation system for, when performing an operation of a minute part of the brain, the heart, etc. of a patient that is an object to be observed, observing the minute part, an optical microscope system including a magnification optical system that magnifies the minute part has been known (e.g. see Patent Literature 1). When performing an operation using the microscope system, an operator such as a medical doctor (the user) performs the operation while observing the surgical site via an eyepiece.

FIG. 10 is a diagram schematically showing a situation in which an operator performs an operation using a conventional optical microscope system. As shown in FIG. 10, an operator 401 performs an operation while observing the surgical site of a patient 402 via an eyepiece 502 of a microscope unit 501. Hence, when the operation time is increased, the burden on the eye of the operator 401 is increased, and also the burden on the body of the operator 401 due to maintaining the same posture is increased.

As a technology to solve such a problem of the optical microscope system, a video microscope system including an imaging means that images a minute part such as a surgical site is known (e.g. see Patent Literature 2). FIG. 11 is a diagram schematically showing a situation in which an operation is performed using a conventional video microscope system. As shown in FIG. 11, an operator 401 performs an operation while observing, with a monitor 602, an image of the surgical site of a patient 402 captured by an imaging unit 601. By such a video microscope system, the burden on the eye and body of the operator in a long-time operation can be greatly reduced as compared to the case of the optical microscope system.

CITATION LIST

Patent Literature

Patent Literature 1: JP 2004-117596A
Patent Literature 2: JP 2002-272760A

DISCLOSURE OF INVENTION

Technical Problem

In the case of the video microscope system, unlike in the optical microscope system, it is desirable that there be few obstructions of the visual field at the time when the operator views the monitor. However, for example in the case shown in FIG. 11, the imaging unit 601 is located between the operator 401 and the monitor 602, and constitutes an obstruction at the time when the operator 401 views the monitor 602. A situation similar to FIG. 11 occurs also in FIG. 2 of Patent Literature 2 described above, etc.

Thus, it is hard to say that measures to ensure the visual field at the time when the operator views the monitor are sufficiently taken in the conventional video microscope system.

The present disclosure has been made in view of the above, and an object of the present disclosure is to provide a medical observation apparatus and a medical observation system with which, when imaging an object to be observed and displaying the image, the user's visual field for observing the displayed image can be sufficiently ensured.

Solution to Problem

In order to solve the above problem and achieve the object, a medical observation apparatus according to the present disclosure includes: a columnar microscope unit configured to image a minute part of an object to be observed with magnification and thereby output an imaging signal; and a support unit including a first joint unit holding the microscope unit in a rotationally movable manner around a first axis parallel to a height direction of the microscope unit, a first arm unit holding the first joint unit and extending in a direction different from the height direction of the microscope unit, a second joint unit holding the first arm unit in a rotationally movable manner around a second axis orthogonal to the first axis, and a second arm unit holding the second joint unit. In a plane passing through the first and second axes, a cross section of the microscope unit, the first and second joint units, and the first and second arm units is included in a circle that has a center at a focus position of the microscope unit and passes through an end point of the first joint unit that is at the maximum distance from the focus position.

In the medical observation apparatus, the second axis may pass through a side that is nearer to the first joint unit than a center in a height direction of a columnar portion composed of the microscope unit and the first joint unit is.

In the medical observation apparatus, a transmission means provided in an interior of the support unit and configured to transmit an imaging signal outputted by the microscope unit may be further included.

In the medical observation apparatus, the transmission means may include a plurality of thin coaxial cables passing through an interior of the first joint unit and configured to transmit an imaging signal outputted by the microscope unit.

In the medical observation apparatus, part of the plurality of thin coaxial cables may extend so as to form a bundle passing through an axis in the height direction of the microscope unit in an interior of the first joint unit.

In the medical observation apparatus, two bundling units individually bundling both end portions of a portion where the plurality of thin coaxial cables extend so as to form a bundle may be further included.

In the medical observation apparatus, a photoelectric conversion means provided in an interior of the support unit and configured to convert an imaging signal outputted by the microscope unit to an optical signal and output the converted signal may be further included.

In the medical observation apparatus, a transmission means provided in an interior of the support unit and configured to transmit an imaging signal outputted by the microscope unit may be further included. The transmission means may include a plurality of thin coaxial cables passing through an interior of the first joint unit, each having one end connected to the microscope unit and the other end connected to the photoelectric conversion means, and configured to transmit an imaging signal outputted by the microscope unit to the photoelectric conversion means.

In the medical observation apparatus, the photoelectric conversion means may be provided in an interior of the first arm unit.

In the medical observation apparatus, a transmission means provided in an interior of the support unit and configured to transmit an imaging signal outputted by the microscope unit may be further included. The transmission means may further include an optical fiber configured to transmit an optical signal converted by the photoelectric conversion means.

In the medical observation apparatus, a manipulation input unit provided on a side surface of the microscope unit and configured to accept a manipulation input to the medical observation apparatus may be further included.

A medical observation system according to the present disclosure includes: the medical observation apparatus described above; a control device configured to perform signal processing on the imaging signal outputted by the microscope unit to create image data for display; and a display device configured to display an image corresponding to image data created by the control device.

Advantageous Effects of Invention

According to the present disclosure, in the plane passing through the first axis that is the rotation axis of the microscope unit and the second axis that is an axis orthogonal to the first axis and is the rotation axis of the first arm unit, the cross section of the microscope unit, the first and second joint units, and the first and second arm units is made to be included in a circle that has the center at the focus position of the microscope unit and passes through an end point of the first joint unit that is at the maximum distance from the focus position; therefore, a configuration in which the first and second arm units and the second joint unit are hidden behind the microscope unit and the first joint unit as viewed from the user can be obtained. Thus, when imaging an object to be observed and displaying the image, the user's visual field for viewing the displayed image can be sufficiently ensured.

MODE(S) FOR CARRYING OUT THE INVENTION

Figure 1:
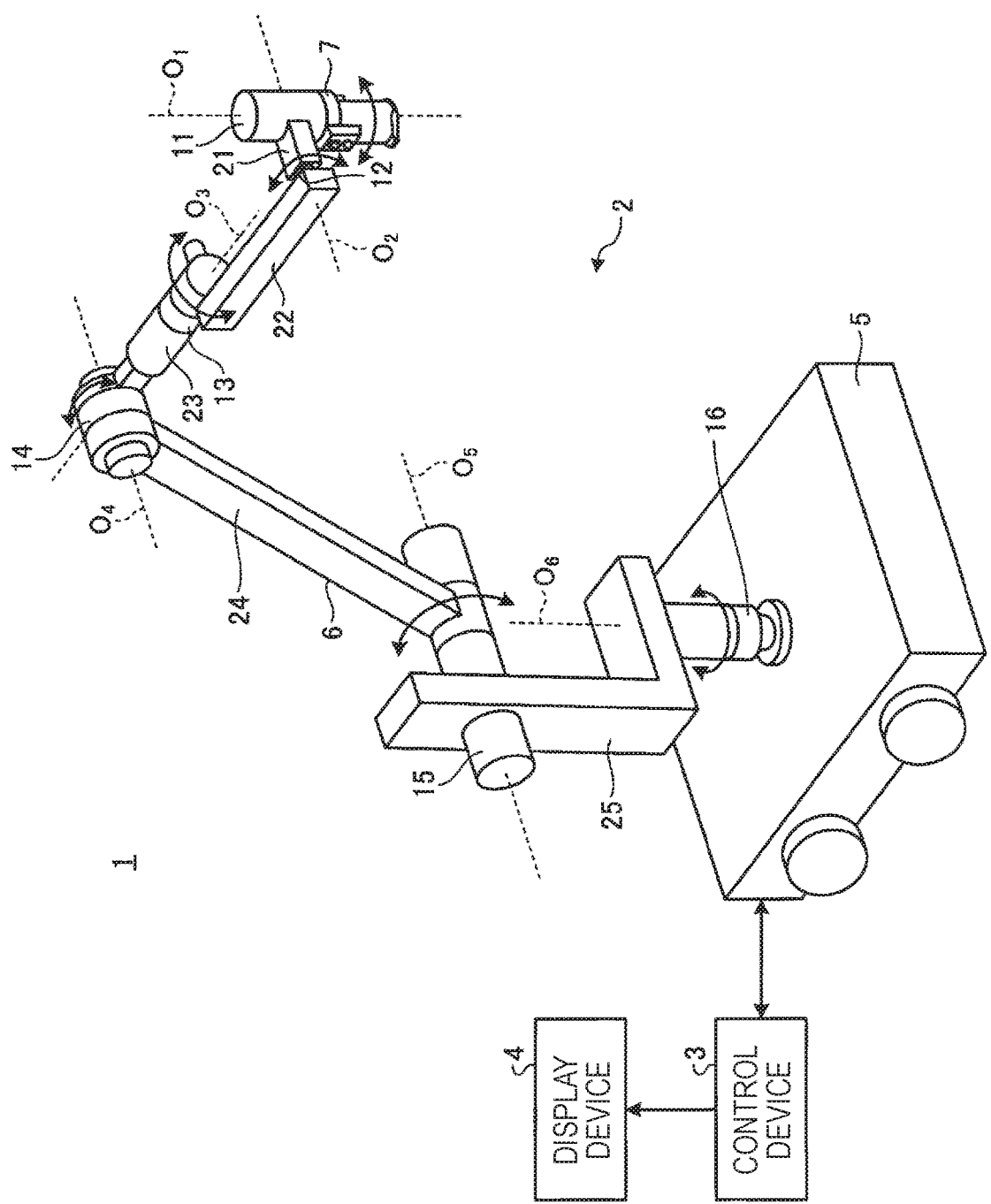
FIG. 1 is a perspective view showing an external configuration of a medical observation system according to Embodiment 1 of the present disclosure.

Hereinbelow, embodiments of the present disclosure (hereinafter, referred to as "embodiments") are described with reference to the appended drawings. The drawings are only schematic ones, and portions for which the relationships between dimensions and the proportions are different among drawings may be included in the drawings.

Embodiment 1

FIG. 1 is a diagram showing the configuration of a medical observation system according to Embodiment 1 of the present disclosure. A medical observation system 1 shown in the drawing includes a medical observation apparatus (hereinafter, referred to as an observation apparatus) 2 having a function as a microscope that images a minute structure of an object to be observed with magnification, a control device 3 that comprehensively controls the operation of the medical observation system 1, and a display device 4 that displays an image captured by the observation apparatus 2.

The observation apparatus 2 includes a base unit 5 capable of moving on the floor surface, a support unit 6 supported by the base unit 5, and a columnar microscope unit 7 that is provided at the tip of the support unit 6 and images a minute part of an object to be observed with magnification.

The support unit 6 includes a first joint unit 11, a first arm unit 21, a second joint unit 12, a second arm unit 22, a third joint unit 13, a third arm unit 23, a fourth joint unit 14, a fourth arm unit 24, a fifth joint unit 15, a fifth arm unit 25, and a sixth joint unit 16.

The support unit 6 includes four sets each of which is composed of two arm units and a joint unit that links one of the two arm units (the tip side) to the other (the root end side) in a rotationally movable manner. The four sets are specifically (the first arm unit 21, the second joint unit 12, the second arm unit 22), (the second arm unit 22, the third joint unit 13, the third arm unit 23), (the third arm unit 23, the fourth joint unit 14, the fourth arm unit 24), and (the fourth arm unit 24, the fifth joint unit 15, the fifth arm unit 25).

The first joint unit 11 holds, on its tip side, the microscope unit 7 in a rotationally movable manner, and is held on its root end side by the first arm unit 21 in a state of being fixed to a tip portion of the first arm unit 21. The first joint unit 11 has a circular cylindrical shape, and holds the microscope unit 7 in a rotationally movable manner around a first axis $O_1$. The first arm unit 21 has a shape extending from the side surface of the first joint unit 11 in a direction orthogonal to the first axis $O_1$. A more detailed configuration of the first joint unit 11 is described later.

The second joint unit 12 holds, on its tip side, the first arm unit 21 in a rotationally movable manner, and is held on its root end side by the second arm unit 22 in a state of being fixed to a tip portion of the second arm unit 22. The second joint unit 12 has a circular cylindrical shape, and holds the first arm unit 21 in a rotationally movable manner around a second axis $O_2$ that is an axis orthogonal to the first axis $O_1$. The second arm unit 22 has a substantially L-shaped configuration, and is linked to the second joint unit 12 in an end portion of the longer line portion of the L shape.

The third joint unit 13 holds, on its tip side, the shorter line portion of the L shape of the second arm unit 22 in a rotationally movable manner, and is held on its root end side by the third arm unit 23 in a state of being fixed to a tip portion of the third arm unit 23. The third joint unit 13 has a circular cylindrical shape, and holds the second arm unit 22 in a rotationally movable manner around a third axis $O_3$ that is an axis orthogonal to the second axis $O_2$ and parallel to the direction in which the second arm unit 22 extends. In the third arm unit 23, the tip side has a circular cylindrical shape, and a hole penetrating in a direction orthogonal to the height direction of the circular cylinder on the tip side is formed on the root end side. The third joint unit 13 is held by the fourth joint unit 14 in a rotationally movable manner via the hole.

The fourth joint unit 14 holds, on its tip side, the third arm unit 23 in a rotationally movable manner, and is held on its root end side by the fourth arm unit 24 in a state of being fixed to the fourth arm unit 24. The fourth joint unit 14 has a circular cylindrical shape, and holds the third arm unit 23 in a rotationally movable manner around a fourth axis $O_4$ that is an axis orthogonal to the third axis $O_3$.

The fifth joint unit 15 holds, on its tip side, the fourth arm unit 24 in a rotationally movable manner, and is, on its root end side, attached fixedly to the fifth arm unit 25. The fifth joint unit 15 has a circular cylindrical shape, and holds the fourth arm unit 24 in a rotationally movable manner around a fifth axis $O_5$ that is an axis parallel to the fourth axis $O_4$. The fifth arm unit 25 is formed of an L-shaped portion and a bar-like portion extending downward from the horizontal line portion of the L shape. The fifth joint unit 15 is, on its root end side, attached to an end portion of the vertical line portion of the L shape of the fifth arm unit 25.

The sixth joint unit 16 holds, on its tip side, the fifth arm unit 25 in a rotationally movable manner, and is, on its root end side, attached fixedly to the upper surface of the base unit 5. The sixth joint unit 16 has a circular cylindrical shape, and holds the fifth arm unit 25 in a rotationally movable manner around a sixth axis $O_6$ that is an axis orthogonal to the fifth axis $O_5$. A root end portion of the bar-like portion of the fifth arm unit 25 is attached to the tip side of the sixth joint unit 16.

The support unit 6 having the configuration described above achieves movements with a total of 6 degrees of freedom, i.e. 3 degrees of freedom of translation and 3 degrees of freedom of rotation, in the microscope unit 7.

The first joint unit 11 to the sixth joint unit 16 include electromagnetic brakes that prohibit the rotational movements of the microscope unit 7 and the first arm unit 21 to the fifth arm unit 25, respectively. Each electromagnetic brake is released in a state where an arm manipulation switch 73 (described later) provided in the microscope unit 7 is pushed, and the rotational movements of the microscope unit 7 and the first arm unit 21 to the fifth arm unit 25 are permitted. An air brake may be used in place of the electromagnetic brake.

Figure 2:
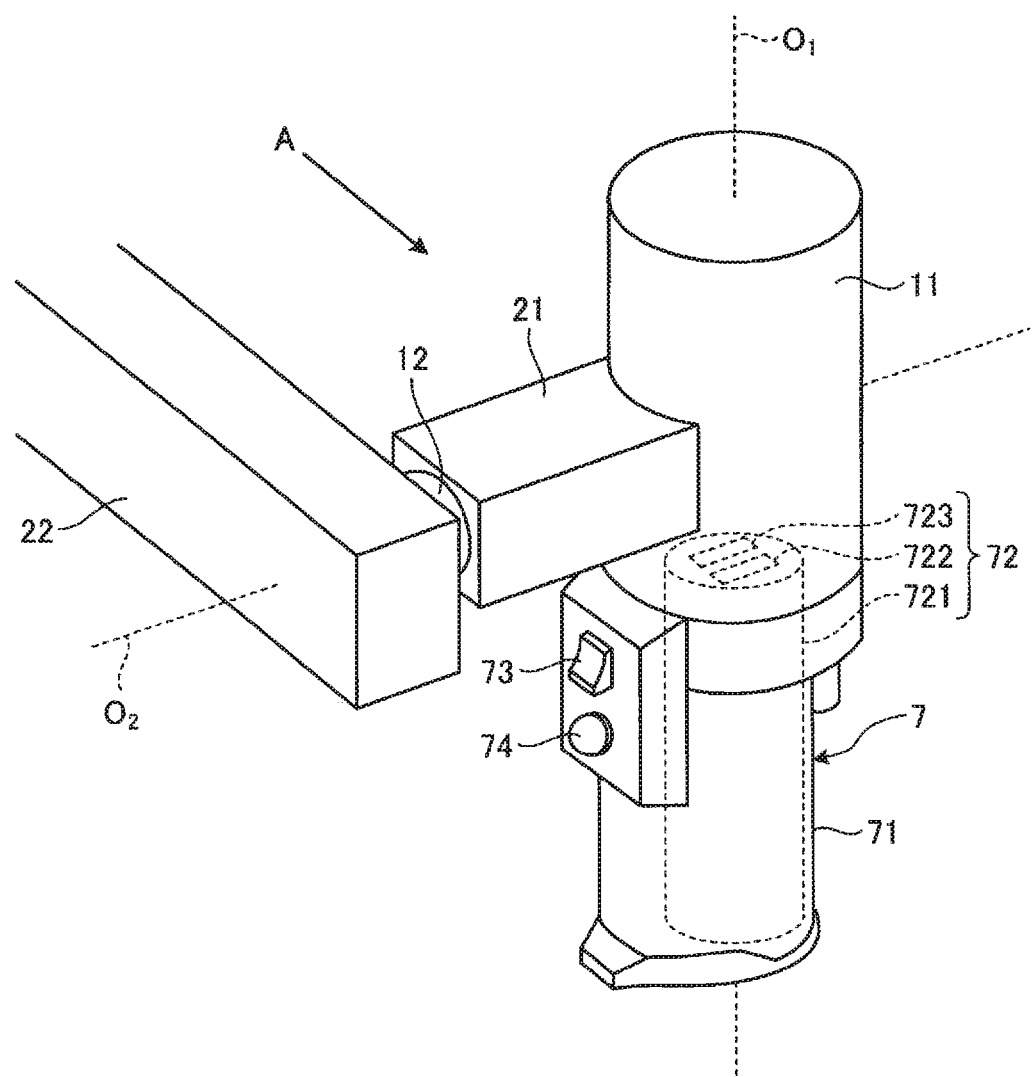
FIG. 2 is an enlarged perspective view showing the configuration of a microscope unit of a medical observation apparatus according to Embodiment 1 of the present disclosure and the vicinity thereof.
Figure 3:
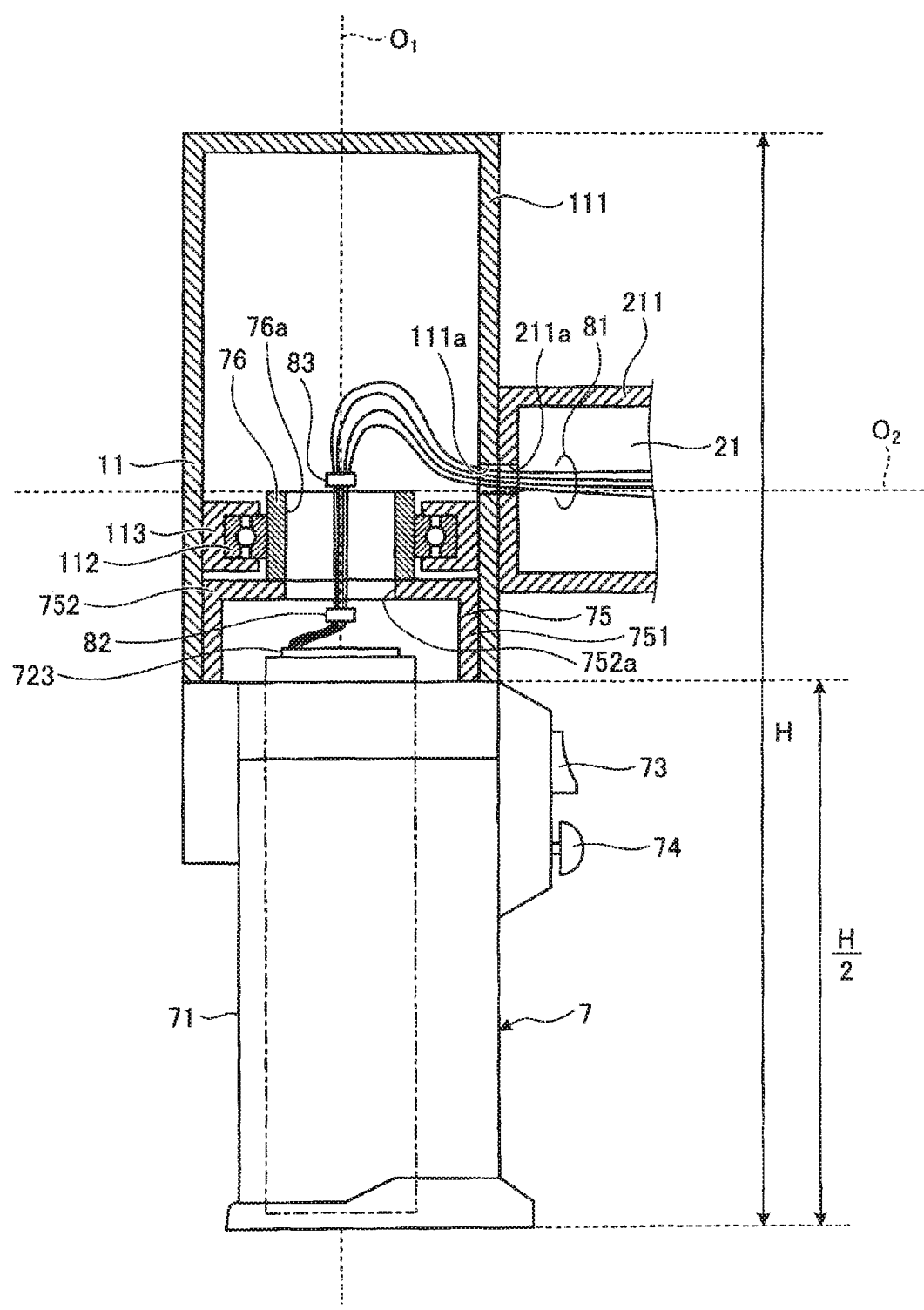
FIG. 3 is a partial cross-sectional view as viewed in the direction of arrow A of FIG. 2.

FIG. 2 is an enlarged perspective view showing the configuration of the microscope unit 7 of the observation apparatus 2 and the vicinity thereof. FIG. 3 is a partial cross-sectional view as viewed in the direction of arrow A of FIG. 2. The configuration of the microscope unit 7 will now be described with reference to FIG. 2 and FIG. 3.

The microscope unit 7 includes a cylindrical unit 71 having a circular cylindrical shape, an imaging unit 72 that is provided in the hollow portion of the cylindrical unit 71 and captures an image of an object to be observed with magnification, an arm manipulation switch 73 that accepts a manipulation input that releases the electromagnetic brakes in the first joint unit 11 to the sixth joint unit 16 to permit the rotational movements of the joint units, a cross lever 74 capable of changing the magnification and the focal distance to the object to be observed in the imaging unit 72, an upper cover 75 formed around an upper portion of the imaging unit 72 and fitted in the first joint unit 11, and an axis unit 76 in a hollow circular cylindrical shape extending from the upper cover 75 along the first axis $O_1$.

The cylindrical unit 71 has a circular cylindrical shape with a diameter smaller than the diameter of the first joint unit 11, and a cover glass that protects the imaging unit 72 is provided on the opening surface at the lower end of the cylindrical unit 71 (not illustrated). The shape of the cylindrical unit 71 is not limited to a circular cylindrical shape, and may be a cylindrical shape in which the cross section orthogonal to the height direction is an ellipse or a polygon, for example.

The imaging unit 72 includes an optical system 721 that includes a plurality of lenses arranged such that their optical axes coincide with the first axis $O_1$ and that collects light from an object to be observed and forms an image, and two imaging elements 722 and 723 each of which receives light collected by the optical system 721 and photoelectrically converts the light to generate an imaging signal. In FIG. 2, only a cylindrical casing that houses the plurality of lenses included in the optical system 721 is described.

The optical system 721 is capable of changing the magnification of an image of the object to be observed and the focal distance to the object to be observed in accordance with the manipulation of the cross lever 74.

Each of the imaging elements 722 and 723 is formed using a charge-coupled device (CCD) or a complementary metal oxide semiconductor (CMOS). The imaging elements 722 and 723 generate two imaging signals having a mutual parallax, as imaging signals for creating a three-dimensional image. The imaging signals are outputted as digital signals individually from the imaging elements 722 and 723.

The arm manipulation switch 73 is a push-button switch. The electromagnetic brakes of the first joint unit 11 to the sixth joint unit 16 are released while the user keeps the arm manipulation switch 73 pushed. The arm manipulation switch 73 is provided on a side surface on the opposite side to the side surface faced by the user during the manipulation of the microscope unit 7, in other words, on a side surface that is the user's blind spot during the manipulation of the microscope unit 7. The arm manipulation switch 73 constitutes a part of a manipulation input unit that accepts a manipulation input to the observation apparatus 2.

The cross lever 74 is manipulable along the height direction of the cylindrical unit 71 and the round direction orthogonal to the height direction. The cross lever 74 is provided on the side surface of the cylindrical unit 71 below the arm manipulation switch 73 along the height direction of the cylindrical unit 71. Also the cross lever 74 constitutes a part of the manipulation input unit that accepts a manipulation input to the observation apparatus 2, similarly to the arm manipulation switch 73.

When the cross lever 74 is manipulated from the position shown in FIG. 2 along the height direction of the cylindrical unit 71, the magnification is changed; and when the cross lever 74 is manipulated from the position shown in FIG. 2 along the round direction of the cylindrical unit 71, the focal distance to the object to be observed is changed. For example, when the cross lever 74 is moved upward along the height direction of the cylindrical unit 71, the magnification is increased; and when the cross lever 74 is moved downward along the height direction of the cylindrical unit 71, the magnification is decreased. Further, when the cross lever 74 is moved clockwise along the round direction of the cylindrical unit 71, the focal distance to the object to be observed is increased; and when the cross lever 74 is moved counterclockwise along the round direction of the cylindrical unit 71, the focal distance to the object to be observed is decreased. The assignment of the direction of movement of the cross lever 74 and manipulation is not limited to that described herein.

The upper cover 75 has a circular cylindrical portion 751 and a hollow discoidal portion 752 provided at the upper end of the circular cylindrical portion 751 and having the same diameter as the circular cylindrical portion 751. The axis unit 76 in a circular cylindrical shape that extends along the first axis $O_1$ and in which a hollow portion 76a communicating with the hollow portion 752a of the hollow discoidal portion 752 is formed is attached to the hollow discoidal portion 752.

Next, the configuration of a main part of the first joint unit 11 is described with reference to FIG. 3. The first joint unit 11 has a circular cylindrical shape in which an upper end portion has a bottom, and includes an outer shell 111 that fits the upper cover 75 of the microscope unit 7 in its inner periphery, an axially supporting unit 112 that axially supports the axis unit 76 of the microscope unit 7 in a rotationally movable manner, and a holding unit 113 that is fixed to the outer shell 111 and fixedly holds the outer periphery of the axially supporting unit 112. The outer shell 111 is fixedly connected to an outer shell 211 of the first arm unit 21. A through hole 111a is formed in a connection portion to the outer shell 211 of the outer shell 111. The through hole 111a communicates with a through hole 211a formed in the outer shell 211. In FIG. 3, the configuration of the electromagnetic brake etc. is omitted.

Figure 4:
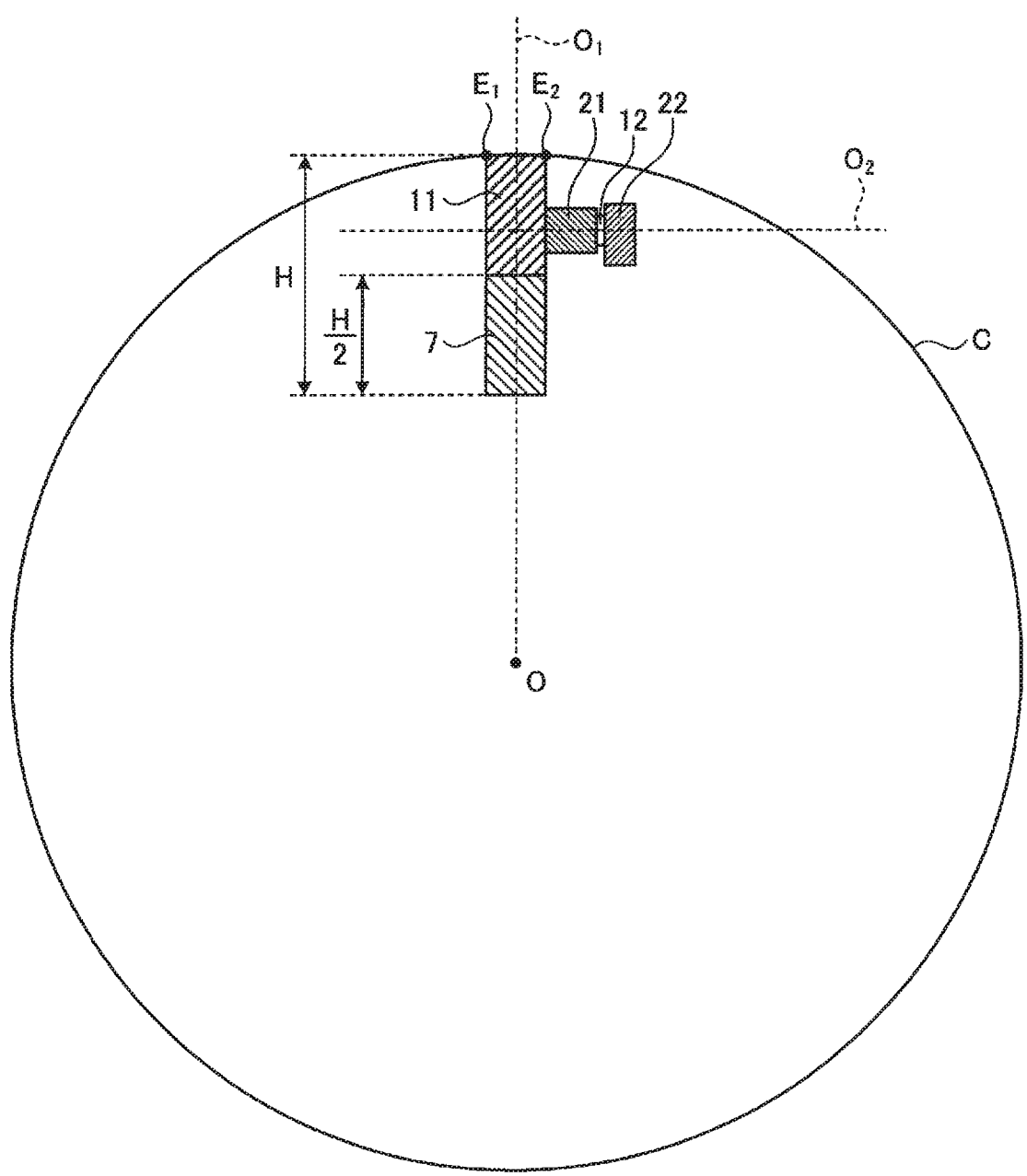
FIG. 4 is a schematic diagram describing a characteristic of a tip portion of the medical observation apparatus according to Embodiment 1 of the present disclosure.

FIG. 4 is a schematic diagram describing a characteristic of a tip portion of the observation apparatus 2. FIG. 4 shows the plane passing through the first axis $O_1$ and the second axis $O_2$. Here, the tip portion of the observation apparatus 2 is composed of the microscope unit 7, the first joint unit 11, the first arm unit 21, the second joint unit 12, and the second arm unit 22. The tip portion of the observation apparatus 2 has a configuration in which, as viewed on the plane passing through the first axis $O_1$ and the second axis $O_2$, the cross section of the tip portion is included in a circle C that has the center at the focus position O of the microscope unit 7 and passes through end points $E_1$ and $E_2$ of the first joint unit 11 that are at the maximum distance from the focus position O. The focus position O of the microscope unit 7 may be variable or fixed. In the case where the focus position O is variable, the tip portion of the observation apparatus 2 is included in a circle that has the center at any given focus position in the variable range and passes through end points $E_1$ and $E_2$ of the first joint unit 11 that are at the maximum distance from the focus position.

In the tip portion of the observation apparatus 2, the second axis $O_2$ passes through a side that is nearer to the first joint unit 11 than the center position in the height direction of a columnar portion composed of the microscope unit 7 and the first joint unit 11 is. In FIG. 3 and FIG. 4, the height of the columnar portion is denoted by H. The center position in the height direction is a position at a distance of H/2 from the lower end of the microscope unit 7. Although in FIG. 3 and FIG. 4 the center position in the height direction is located at the boundary between the microscope unit 7 and the outer peripheral surface of the first joint unit 11, this is only an example.

Figure 5:
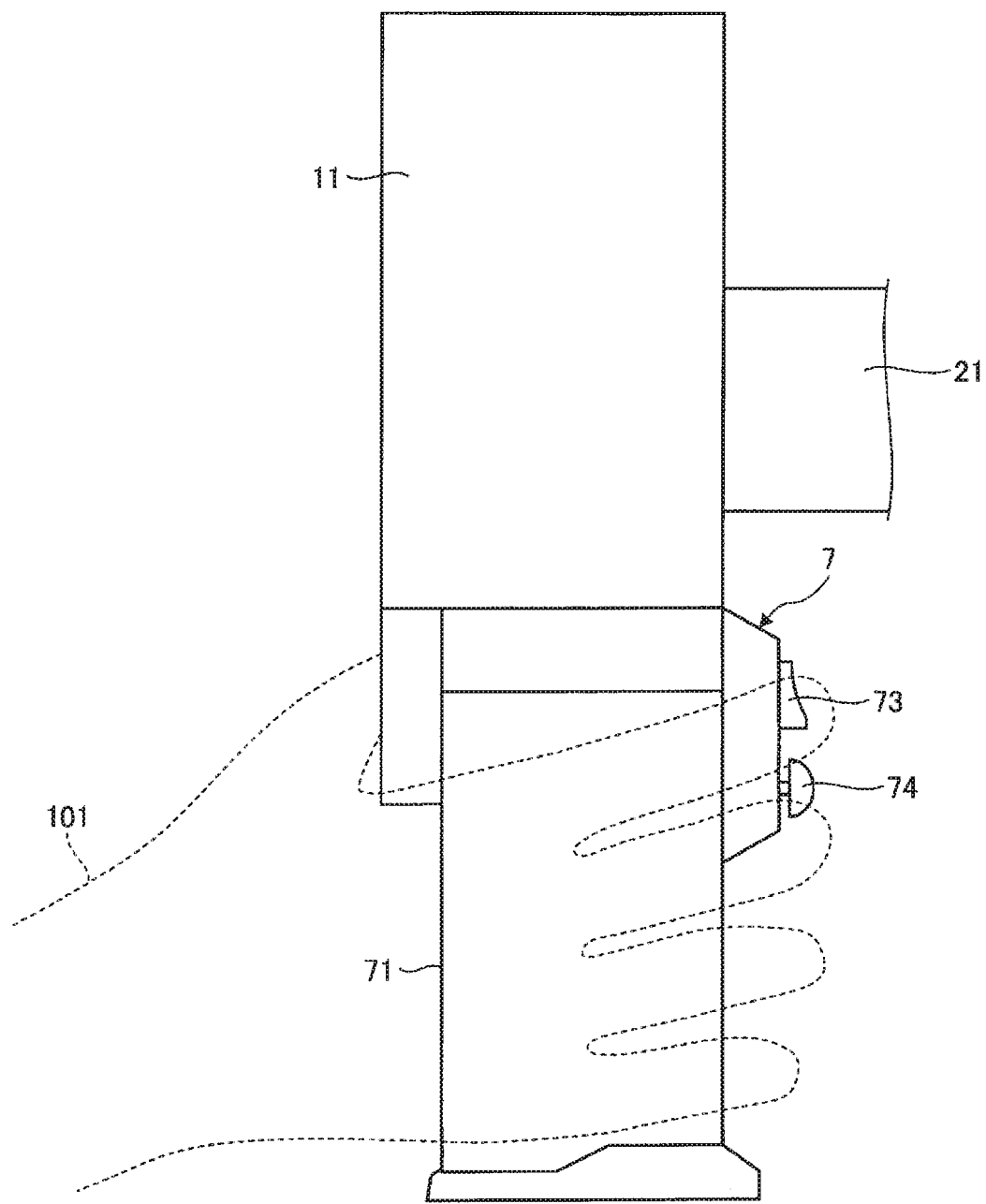
FIG. 5 is a diagram schematically showing a situation where a user manipulates the microscope unit of the medical observation apparatus according to Embodiment 1 of the present disclosure.

FIG. 5 is a diagram schematically showing a situation where a user manipulates the microscope unit 7. The user manipulates the microscope unit 7 while facing, of the side surface of the cylindrical unit 71, a side surface (the left side surface of FIG. 5) on the opposite side to the side surface (the right side surface of FIG. 5) on which the arm manipulation switch 73 is provided. In this event, the user manipulates the support unit 6 while, in a state of grasping the microscope unit 7 with the right hand 101, keeping the arm manipulation switch 73 pushed with the index finger (or the middle finger or the ring finger).

The tip portion of the observation apparatus 2 has the feature of the shape described with reference to FIG. 4; therefore, when the user manipulates the microscope unit 7, the tip portion of the first arm unit 21, the second joint unit 12, and the second arm unit 22 is always located behind the microscope unit 7 and the first joint unit 11 as viewed from the user, and is less likely to enter the user's visual field. Therefore, the proportion of the tip portion of the observation apparatus 2 in the user's visual field can be reduced, and the obstruction of the user's visual field can be prevented.

In the observation apparatus 2, the user can manipulate the support unit 6 by pushing the arm manipulation switch 73 while naturally grasping the microscope unit 7. In particular, since the arm manipulation switch 73 is provided on, of the side surface of the microscope unit 7, a side surface that is the user's blind spot (a side surface on the opposite side to the side surface faced by the user), the user can perform the manipulation of continuously pushing the arm manipulation switch 73 and the manipulation of pushing and releasing the arm manipulation switch 73 without a sense of incongruity even when the user rotates or tilts the microscope unit 7 in a state of grasping the microscope unit 7 with the hand.

Furthermore, in the observation apparatus 2, it is not necessary to provide a grip unit including the arm manipulation switch 73 separately, and the microscope unit 7 can be configured in a small size; thus, the user's visual field can be sufficiently ensured.

Furthermore, in the observation apparatus 2, since the user grasps the periphery of the microscope unit 7 with the hand, the user can intuitively recognize the position of the optical axis of the optical system 721, that is, the direction of the imaging visual field, and can move the microscope unit 7 to a desired position easily; thus, manipulability is excellent.

Next, the configuration for the transmission of imaging signals outputted by the imaging unit 72 is described with reference to FIG. 3. A plurality of thin coaxial cables that are a transmission means for transmitting imaging signals extend from each of the imaging elements 722 and 723, and all the cables constitute a cable group 81. The cable group 81 passes through the hollow portion 76a of the axis unit 76. The cable group 81 is bundled by bundling units 82 and 83 individually on the outside of both end sides of the axis unit 76. Hence, the cable group 81 forms a bundle between the bundling unit 82 and the bundling unit 83. The bundle portion of the cable group 81 passes through the first axis $O_1$. The cable group 81 extends from the first joint unit 11 to the first arm unit 21 via the through hole 111a of the outer shell 111 and the through hole 211a of the outer shell 211.

Thus, by bundling the cable group 81 with the two bundling units 82 and 83, the occurrence of a twist due to the rotational movement of the microscope unit 7 relative to the first joint unit 11 (the first arm unit 21) is suppressed in the bundled bundle portion.

The configuration of the medical observation system 1 will now be further described.

The control device 3 receives imaging signals outputted by the observation apparatus 2, and performs a prescribed signal processing on the imaging signals to create three-dimensional image data for display. The control device 3 is configured using a central processing unit (CPU), a read-only memory (ROM), a random access memory (RAM), etc. The control device 3 may be installed in the base unit 5 and integrated with the observation apparatus 2.

The display device 4 receives three-dimensional image data created by the control device 3 from the control device 3, and displays a three-dimensional image corresponding to the three-dimensional image data. The display device 4 like this includes a liquid crystal display panel or an organic electro-luminescence (EL) display panel.

Figure 6:
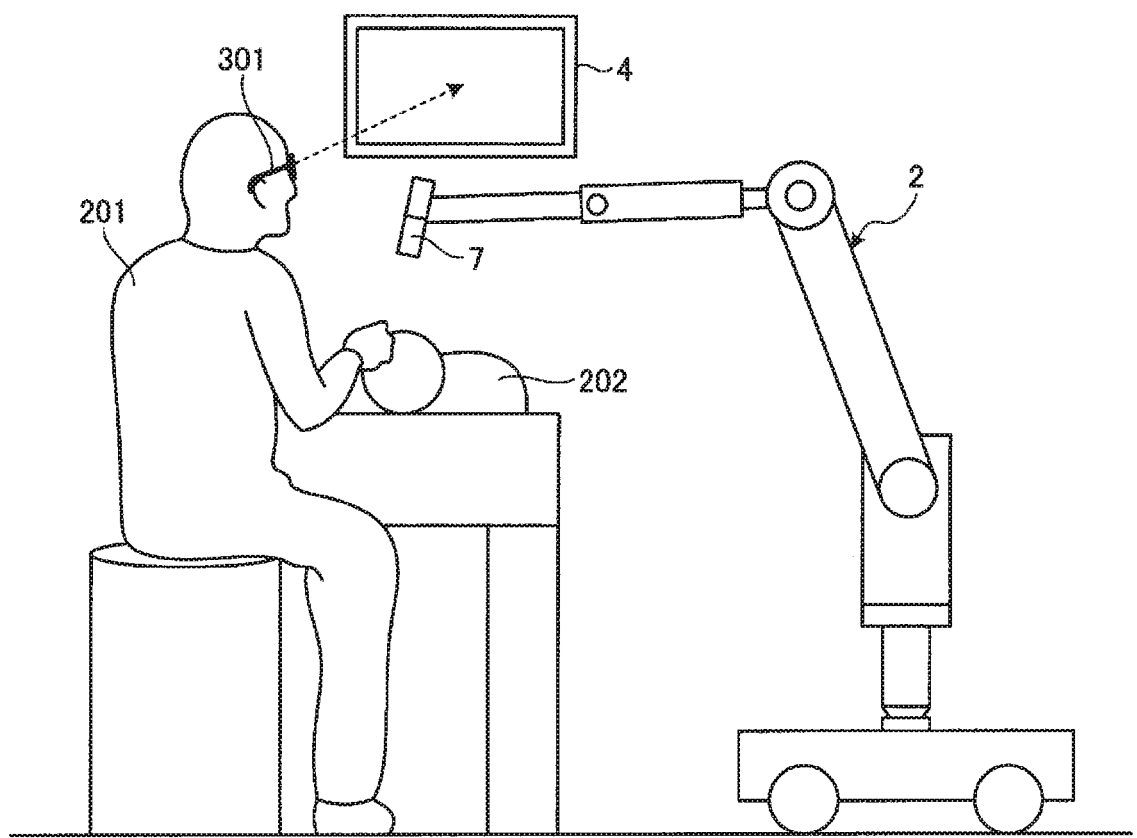
FIG. 6 is a diagram schematically showing a situation of an operation performed using the medical observation system according to Embodiment 1 of the present disclosure.

Next, an overview of an operation performed using the medical observation system 1 having the above configuration is described. FIG. 6 is a diagram schematically showing a situation of an operation using the medical observation system 1. Specifically, FIG. 6 is a diagram schematically showing a situation in which an operator 201 who is the user performs an operation on the head of a patient 202 that is an object to be observed. While wearing eyeglasses 301 for three-dimensional images and visually observing a three-dimensional image displayed by the display device 4, the operator 201 grasps the microscope unit 7 and moves it to a desired position in a state of keeping the arm manipulation switch 73 of the microscope unit 7 pushed, and determines the imaging visual field of the microscope unit 7; then, removes the fingers from the arm manipulation switch 73. Thereby, the electromagnetic brake works in the first joint unit 11 to the sixth joint unit 16, and the imaging visual field of the microscope unit 7 is fixed. After that, the operator 201 performs the adjustment of the magnification and the focal distance to the object to be observed, etc. Since the display device 4 displays a three-dimensional image, the operator 201 can grasp the surgical site stereoscopically through the three-dimensional image.

In order that the operator 201 can grasp the microscope unit 7 easily and the visual field at the time when the operator 201 views the display device 4 or the surgical site of the patient 202 may not be obstructed, it is preferable that, for example, the outer diameter of the cylindrical unit 71 be approximately 40 to 70 mm, the distance between the focus position O of the microscope unit 7 and the lower end of the microscope unit 7 be approximately 150 to 600 mm, and the total height of the microscope unit 7 and the first joint unit 11 be approximately 100 to 220 mm.

In Embodiment 1 of the present disclosure described above, in the plane passing through the first axis $O_1$ and the second axis $O_2$, the cross section of the microscope unit 7, the first joint unit 11, the first arm unit 21, the second joint unit 12, and the second arm unit 22 is made to be included in a circle C that has the center at the focus position O of the microscope unit 7 and passes through end points $E_1$ and $E_2$ of the first joint unit 11 that are at the maximum distance from the focus position O; therefore, a configuration in which the first arm unit 21, the second joint unit 12, and the second arm unit 22 are hidden behind the microscope unit 7 and the first joint unit 11 as viewed from the user can be obtained. Thus, when imaging an object to be observed and displaying the image, the user's visual field for viewing the displayed image can be sufficiently ensured.

Furthermore, in the Embodiment 1, since the second axis $O_2$ passes through a side that is nearer to the first joint unit 11 than the center in the height direction of the columnar portion composed of the microscope unit 7 and the first joint unit 11 is, the portion that the user grasps can be sufficiently ensured without increasing the size of the tip portion. Therefore, an observation apparatus 2 having a tip portion shape that is optimal in manipulability and suitable for downsizing can be provided.

Furthermore, in the Embodiment 1, since a part of the cable group 81 is made to form a bundle and pass through the first axis $O_1$, the occurrence of a twist due to the rotational movement of the microscope unit 7 relative to the first joint unit 11 can be suppressed in this portion. In particular, in the case where the bundle portion is formed using the two bundling units 82 and 83, the bundle portion rarely experiences a twist.

Furthermore, in the Embodiment 1, since the cable group 81 is provided in the interior of the support unit 6, the user's visual field is not obstructed as compared to the case where the cable group 81 is drawn outside the support unit 6, and the user's visual field can be ensured in a sufficiently large range. Here, in the Embodiment 1, a sterile drape may be provided so as to cover the surface of the observation apparatus 2 in order to keep the sterile state of the observation apparatus 2. In the case of using a sterile drape, if the cable group 81 is exposed to the outside of the support unit 6, the outer diameter of each part of the observation apparatus 2 is further increased, and the visual field between the user and the display device 4 is obstructed and the observation by the user becomes difficult. In contrast, in the Embodiment 1, since the cable group 81 is provided in the interior of the support unit 6, the user's visual field can be sufficiently ensured even in the case of using a sterile drape.

Furthermore, in the Embodiment 1, since the user grasps the microscope unit 7 with the hand, the user can intuitively recognize the direction of the optical axis of the optical system 721 or the imaging visual field of the microscope unit 7, and can move the microscope unit 7 to a desired position easily. This is a very advantageous effect as compared to a case like a conventional operating microscope in which a grip provided with a switch for manipulation signal input is apart from the optical axis of the optical system and the optical axis direction cannot be intuitively recognized.

Furthermore, in the Embodiment 1, since the support unit 6 is configured such that a plurality of arm units and joint units are linked, various movements of the microscope unit 7 can be achieved by a simpler configuration than a link mechanism like conventional ones.

Embodiment 2

Figure 7:
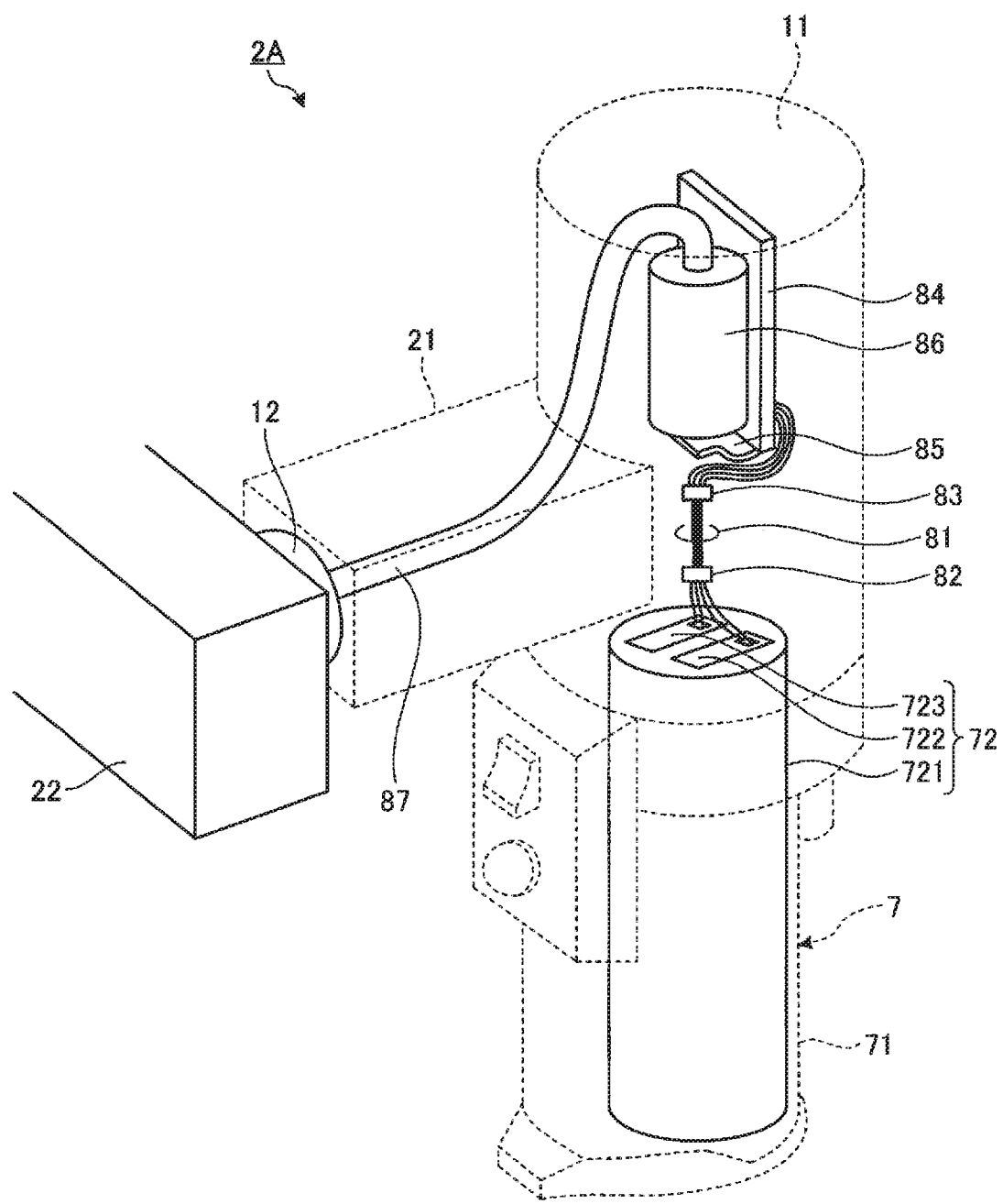
FIG. 7 is a partial cross-sectional view showing the configuration of a main part of a medical observation apparatus according to Embodiment 2 of the present disclosure.

FIG. 7 is a diagram showing the configuration of a main part of an observation apparatus included in a medical observation system according to Embodiment 2 of the present disclosure. More specifically, FIG. 7 is a diagram showing the configuration of a main part of an observation apparatus 2A included in a medical observation system according to the Embodiment 2. The configuration of the medical observation system other than that shown in FIG. 7 is similar to the configuration of the medical observation system 1 described in Embodiment 1.

In the observation apparatus 2A, the cable group 81 is connected to a field-programmable gate array (FPGA) board 84 provided in the interior of the first joint unit 11. The FPGA board 84 is connected to a photoelectric composite module 86 via a flexible board 85 in the interior of the first joint unit 11.

The photoelectric composite module 86 includes a photoelectric conversion element that converts an imaging signal transmitted via the cable group 81 to an optical signal and outputs the converted signal. Further, the photoelectric composite module 86 relays electrical signals such as a control signal and a signal for electric power supply. The photoelectric composite module 86 like this has a circular cylindrical shape, and its bottom surface on the tip side is provided with a connection unit for connecting the flexible board 85. Further, the photoelectric composite module 86 includes a board on which a photoelectric conversion element that converts an imaging signal transmitted via the flexible board 85 to an optical signal and outputs the converted signal is mounted and a board for relaying electrical signals for control and electric power. These boards are housed in a cover member in a circular cylindrical shape. The shape of the cover member of the photoelectric composite module 86 is not limited to a circular cylindrical shape, and may be a cylindrical shape in which the cross section orthogonal to the height direction is an ellipse or a polygon, for example.

The FPGA board 84, the flexible board 85, and the photoelectric composite module 86 have a function as a photoelectric conversion means that converts an imaging signal outputted by the microscope unit 7 to an optical signal and outputs the converted signal.

One end (the tip) of a composite cable 87 that is a transmission means for transmitting optical signals and electrical signals is connected to the root end side of the photoelectric composite module 86. The composite cable 87 extends from the first joint unit 11 to the first arm unit 21 via the through hole 111a of the outer shell 111 and the through hole 211a of the outer shell 211 (see FIG. 3). The composite cable 87 is provided in the interior of the first arm unit 21 to the fifth arm unit 25, and the other end (the root end) of the composite cable 87 is connected to the control device 3. In the composite cable 87, one or a plurality of optical fibers are placed on the center axis, and a plurality of metal wires are placed around the optical fiber(s). The optical fiber is connected to the board of the photoelectric composite module 86 on which a photoelectric conversion element is mounted, and transmits an optical signal obtained by photoelectrically converting an imaging signal. On the other hand, the metal wire is connected to the board for relaying electrical signals of the photoelectric composite module 86, and transmits electrical signals for control and electric power. In order to suppress the voltage drop during signal transmission in the metal wire, the diameter of the metal wire is preferably set as large as possible.

In Embodiment 2 of the present disclosure described above, when imaging an object to be observed and displaying the image, the user's visual field for viewing the displayed image can be sufficiently ensured, like in Embodiment 1.

Furthermore, in the Embodiment 2, since a photoelectric conversion means (including the FPGA board 84, the flexible board 85, and the photoelectric composite module 86) that converts an imaging signal outputted by the microscope unit 7 to an optical signal and outputs the converted signal is provided in the interior of the first joint unit 11, large-capacity data transmission in which the degradation and dullness of a signal are prevented by using an optical signal and unnecessary radiation is suppressed is enabled. Therefore, it becomes possible to adapt to higher pixels (densification) of the imaging elements 722 and 723.

Furthermore, in the Embodiment 2, since a photoelectric conversion means is provided in the interior of the first joint unit 11 nearest to the microscope unit 7, the degradation of signal quality due to the transmission of electrical signals can be suppressed to a minimum.

Furthermore, in the Embodiment 2, since electrical signals are allowed to be transmitted by the cable group 81 composed of a plurality of thin coaxial cables each having a smaller diameter than a conventional metal wire, the size of the tip portion can be made smaller than in the case of using a conventional metal wire.

Furthermore, in the Embodiment 2, since the composite cable 87 that transmits an optical signal is provided in the interior of the support unit 6, the user's visual field is not obstructed as compared to the case where the composite cable 87 is drawn outside the support unit 6, and the user's visual field can be ensured in a sufficiently large range.

Embodiment 3

Figure 8:
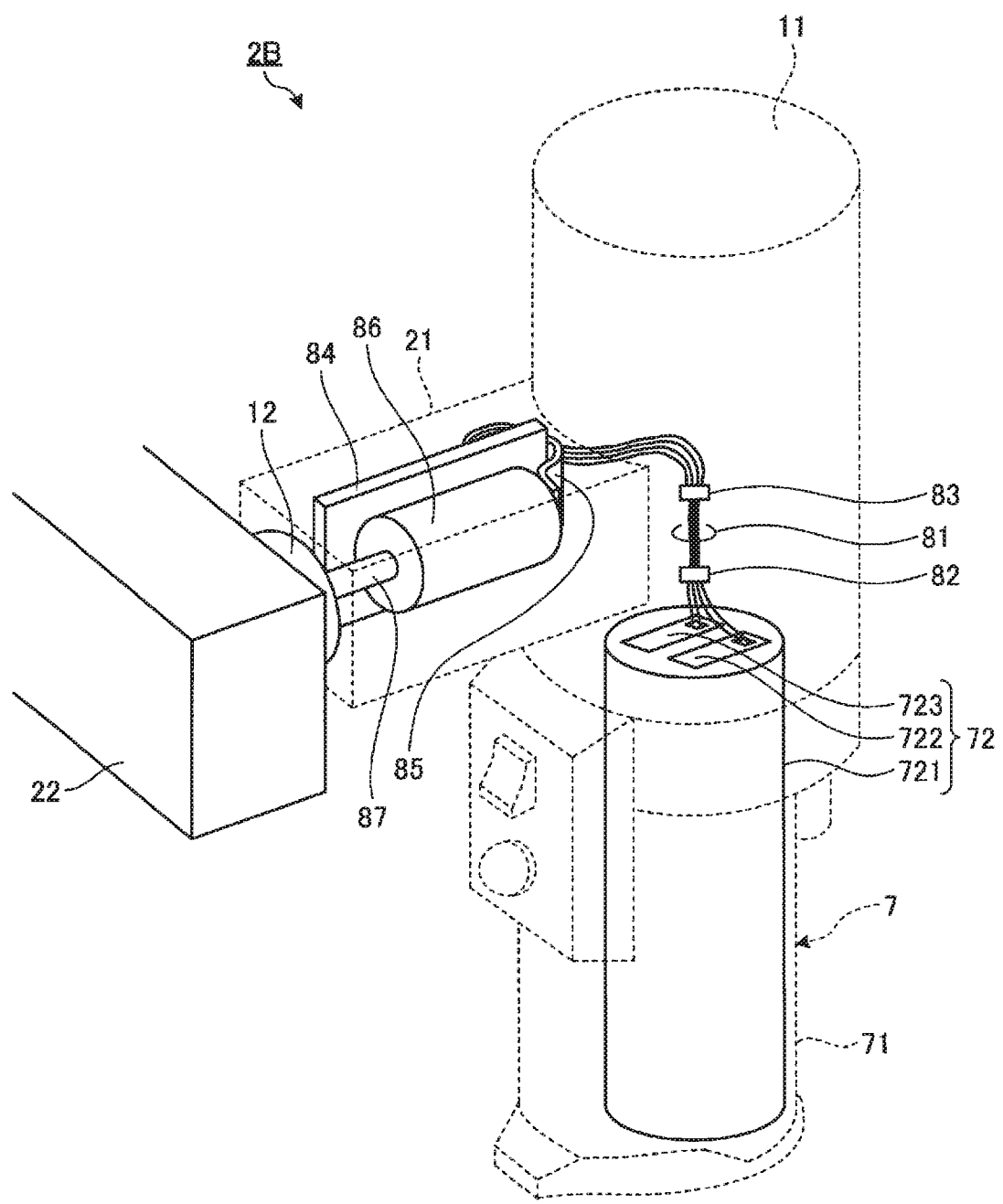
FIG. 8 is a diagram showing the configuration of a main part of an observation apparatus included in a medical observation system according to Embodiment 3 of the present disclosure.

FIG. 8 is a diagram showing the configuration of a main part of an observation apparatus included in a medical observation system according to Embodiment 3 of the present disclosure. More specifically, FIG. 8 is a diagram showing the configuration of a main part of an observation apparatus 2B included in a medical observation system according to the Embodiment 3. The configuration of the medical observation system other than that shown in FIG. 8 is similar to the configuration of the medical observation system 1 described in Embodiment 1.

In the observation apparatus 2B, the cable group 81 is connected to the FPGA board 84 provided in the interior of the first arm unit 21. The FPGA board 84 is connected to the photoelectric composite module 86 via the flexible board 85 in the interior of the first arm unit 21. One end (the tip) of the composite cable 87 that is a transmission means for transmitting optical signals and electrical signals is connected to the root end side of the photoelectric composite module 86. The composite cable 87 is provided in the interior of the second arm unit 22 to the fifth arm unit 25, and the other end (the root end) of the composite cable 87 is connected to the control device 3.

In Embodiment 3 of the present disclosure described above, when imaging an object to be observed and displaying the image, the user's visual field for viewing the displayed image can be sufficiently ensured, like in Embodiment 1.

Furthermore, in the Embodiment 3, since electrical signals are allowed to be transmitted by connecting the imaging unit 72 of the microscope unit 7 and the photoelectric composite module 86 by means of the cable group 81 composed of a plurality of thin coaxial cables, the size of the tip portion can be made smaller than in the case of using a conventional metal wire.

Furthermore, in the Embodiment 3, since a photoelectric conversion means (including the FPGA board 84, the flexible board 85, and the photoelectric composite module 86) that converts an imaging signal outputted by the microscope unit 7 to an optical signal and outputs the converted signal is provided in the interior of the first arm unit 21, large-capacity data transmission using an optical signal is enabled, and it becomes possible to adapt to higher pixels (densification) of the imaging elements 722 and 723. In addition, in the Embodiment 3, since a photoelectric conversion means is not provided in the first joint unit 11, the first joint unit 11 can be further downsized to the extent that the configuration described using FIG. 4 is satisfied.

Embodiment 4

Figure 9:
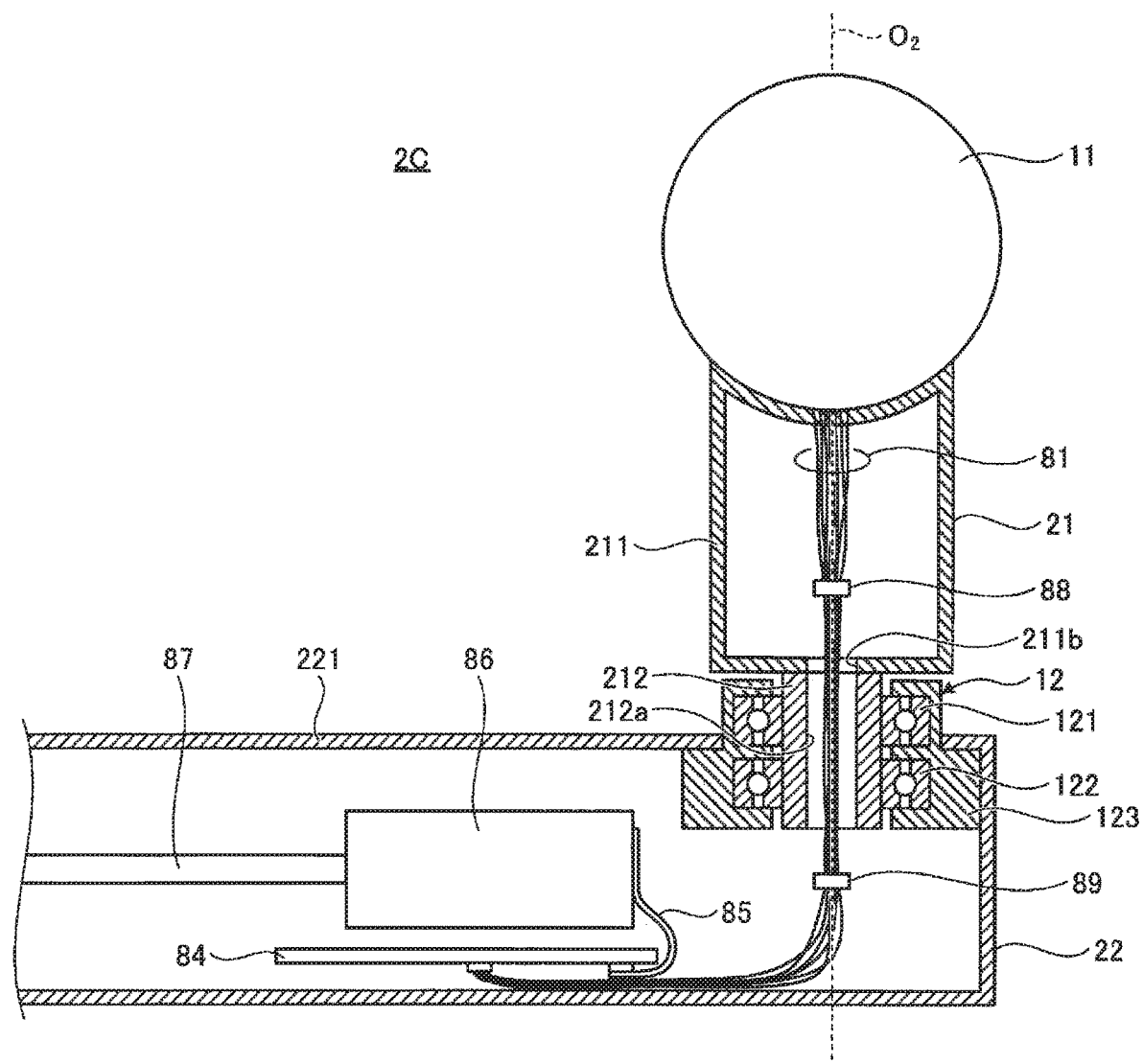
FIG. 9 is a partial cross-sectional view showing the configuration of a main part of an observation apparatus included in a medical observation system according to Embodiment 4 of the present disclosure.
Figure 10:
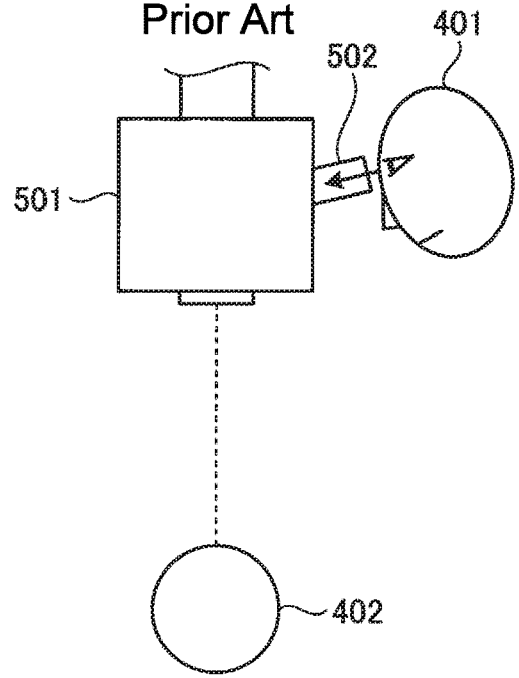
FIG. 10 is a diagram schematically showing a situation where an operator performs an operation using a conventional optical microscope system.
Figure 11:
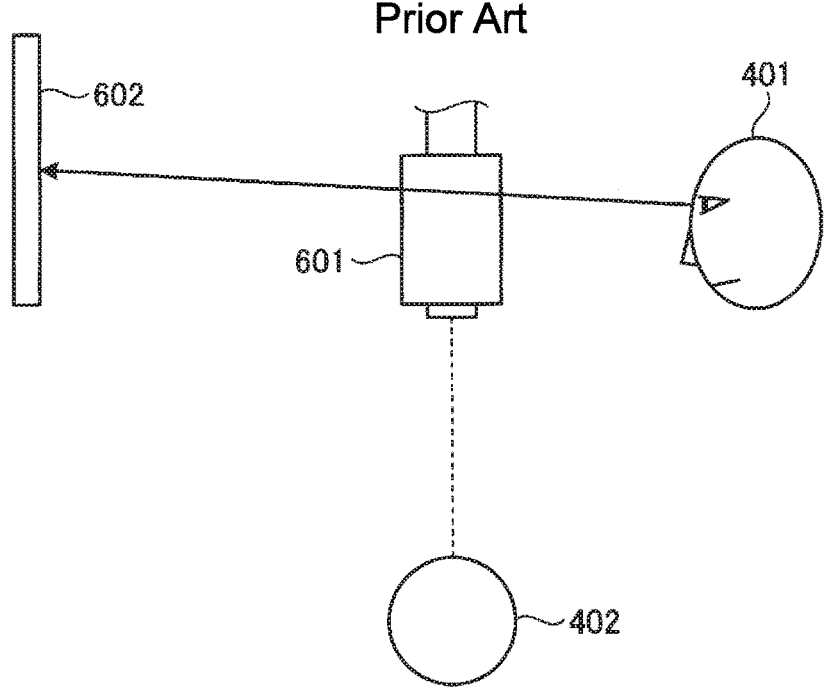
FIG. 11 is a diagram schematically showing a situation where an operator performs an operation using a conventional video microscope system.

FIG. 9 is a partial cross-sectional view showing the configuration of a main part of an observation apparatus included in a medical observation system according to Embodiment 4 of the present disclosure. More specifically, FIG. 9 is a diagram showing the configuration of a main part of an observation apparatus included in a medical observation system according to the Embodiment 4. The configuration of the medical observation system other than that shown in FIG. 9 is similar to the configuration of the medical observation system 1 described in Embodiment 1.

The configuration of a main part of the first arm unit 21, the second joint unit 12, and the second arm unit 22 included in an observation apparatus 2C will now be described with reference to FIG. 9.

In the observation apparatus 2C, the cable group 81 composed of a plurality of thin coaxial cables extending from the first joint unit 11 to the first arm unit 21 further extends from the first arm unit 21 to the interior of the second arm unit 22 via the second joint unit 12. The first arm unit 21 includes the outer shell 211 fixedly attached to the first joint unit 11 and an axis unit 212 in a hollow circular cylindrical shape that extends along the second axis $O_2$ on the root end side of the outer shell 211 and in which a hollow portion 212a communicating with a hollow portion 211b formed in a root end portion of the outer shell 211 is formed.

The second joint unit 12 includes two axially supporting units 121 and 122 that axially support the axis unit 212 in a rotationally movable manner and a holding unit 123 that is fixedly attached to an outer shell 221 of the second arm unit 22 and fixedly holds the outer peripheries of the axially supporting units 121 and 122. In FIG. 7, the configuration of the electromagnetic brake included in the second joint unit 12 etc. is omitted.

The cable group 81 passes through the hollow portion 212a of the first arm unit 21, and extends to the interior of the second arm unit 22. The cable group 81 is bundled by bundling units 88 and 89 individually on the outside of both end sides of the axis unit 212. The cable group 81 forms a bundle between the bundling unit 88 and the bundling unit 89. The bundle portion of the cable group 81 passes through the second axis $O_2$.

Thus, by bundling the cable group 81 with the two bundling units 88 and 89, the occurrence of a twist of the cable group 81 due to the rotational movement of the first arm unit 21 relative to the second joint unit 12 (the second arm unit 22) is suppressed in the bundled bundle portion.

The thin coaxial cables constituting the cable group 81 are connected to an electrode of the FPGA board 84 that is provided on the root end side with respect to the bundling unit 89 in the interior of the second arm unit 22. The FPGA board 84 is connected to the photoelectric composite module 86 via the flexible board 85. An optical signal obtained by the conversion of an imaging signal by the photoelectric composite module 86 is transmitted to the control device 3 via the composite cable 87. Also in the Embodiment 4, the FPGA board 84, the flexible board 85, and the photoelectric composite module 86 have a function as a photoelectric conversion means.

In Embodiment 4 of the present disclosure described above, when imaging an object to be observed and displaying the image, the user's visual field for viewing the displayed image can be sufficiently ensured, like in Embodiment 1.

Furthermore, in the Embodiment 4, since a photoelectric conversion means (including the FPGA board 84, the flexible board 85, and the photoelectric composite module 86) that converts an imaging signal outputted by the microscope unit 7 to an optical signal and outputs the converted signal is provided in the interior of the second arm unit 22, large-capacity data transmission using an optical signal is enabled, and it becomes possible to adapt to higher pixels (densification) of the imaging elements 722 and 723. In addition, in the Embodiment 4, since a photoelectric conversion means is not provided in the first joint unit 11, the first joint unit 11 can be further downsized to the extent that the configuration described using FIG. 4 is satisfied.

Furthermore, in the Embodiment 4, since a part of the cable group 81 is made to form a bundle and pass through the second axis $O_2$, the occurrence of a twist due to the rotational movement of the first arm unit 21 relative to the second joint unit 12 (the second arm unit 22) can be suppressed in this portion. In particular, in the case where the bundle portion is formed using the two bundling units 88 and 89, the bundle portion rarely experiences a twist.

Furthermore, in the Embodiment 4, since a photoelectric conversion means is not provided in the first arm unit 21, the first arm unit 21 can be made shorter than in Embodiment 3, and further downsizing can be achieved.

OTHER EMBODIMENTS

Hereinabove, embodiments of the present disclosure are described; but the present disclosure is not limited to Embodiments 1 to 4 described above. For example, two photoelectric composite modules 86 individually connected to the imaging elements 722 and 723 may be provided in the interior of the support unit 6. In this case, the two photoelectric composite modules 86 may be arranged side by side along the direction in which the first arm unit 21 or the second arm unit 22 extends, or may be arranged in parallel in a direction orthogonal to the direction in which the first arm unit 21 or the second arm unit 22 extends.

The photoelectric composite module 86 may be provided in any of the third arm unit 23 to the fifth arm unit 25. In this case, the first arm unit 21 and the second arm unit 22 located near to the microscope unit 7 can be considerably downsized. In this case, it is preferable that the bundle portion described in Embodiment 1 etc. be formed in a joint unit through which a plurality of thin coaxial cables pass.

The FPGA board 84, the flexible board 85, and the photoelectric composite module 86 may be integrated to form a photoelectric conversion means.

The support unit 6 may include at least one set composed of two arm units and a joint unit that links one of the two arm units to the other in a rotationally movable manner.

Also a configuration in which the imaging unit 72 includes one or three or more imaging elements is possible. In this case, when the imaging unit 72 includes only one imaging element, the display device 4 displays two-dimensional images.

The manipulation input unit provided in the cylindrical unit 71 is not limited to that described above. For example, a manipulation unit for changing the magnification and a manipulation unit for changing the focal distance to the object to be observed may be provided separately.

Also a configuration in which the medical observation apparatus is placed to be hung from the ceiling of the installation place is possible.

Thus, the present disclosure may include various embodiments etc. without departing from the technical idea described in the claims.

Additionally, the present technology may also be configured as below.

(1)

A medical observation apparatus including:

a columnar microscope unit configured to image a minute part of an object to be observed with magnification and thereby output an imaging signal; and a support unit including a first joint unit holding the microscope unit in a rotationally movable manner around a first axis parallel to a height direction of the microscope unit, a first arm unit holding the first joint unit and extending in a direction different from the height direction of the microscope unit, a second joint unit holding the first arm unit in a rotationally movable manner around a second axis orthogonal to the first axis, and a second arm unit holding the second joint unit, wherein, in a plane passing through the first and second axes, a cross section of the microscope unit, the first and second joint units, and the first and second arm units is included in a circle that has a center at a focus position of the microscope unit and passes through an end point of the first joint unit that is at the maximum distance from the focus position.

(2)

The medical observation apparatus according to (1), wherein the second axis passes through a side that is nearer to the first joint unit than a center in a height direction of a columnar portion composed of the microscope unit and the first joint unit is.

(3)

The medical observation apparatus according to (1) or (2), further including a transmission means provided in an interior of the support unit and configured to transmit an imaging signal outputted by the microscope unit.

(4)

The medical observation apparatus according to (3), wherein the transmission means includes a plurality of thin coaxial cables passing through an interior of the first joint unit and configured to transmit an imaging signal outputted by the microscope unit.

(5)

The medical observation apparatus according to (4), wherein part of the plurality of thin coaxial cables extend so as to form a bundle passing through an axis in the height direction of the microscope unit in an interior of the first joint unit.

(6)

The medical observation apparatus according to (5), further including two bundling units individually bundling both end portions of a portion where the plurality of thin coaxial cables extend so as to form a bundle.

(7)

The medical observation apparatus according to any one of (1) to (6), further including a photoelectric conversion means provided in an interior of the support unit and configured to convert an imaging signal outputted by the microscope unit to an optical signal and output the converted signal.

(8)

The medical observation apparatus according to (7), further including a transmission means provided in an interior of the support unit and configured to transmit an imaging signal outputted by the microscope unit, wherein the transmission means includes a plurality of thin coaxial cables passing through an interior of the first joint unit, each having one end connected to the microscope unit and the other end connected to the photoelectric conversion means, and configured to transmit an imaging signal outputted by the microscope unit to the photoelectric conversion means.

(9)

The medical observation apparatus according to (7) or (8), wherein the photoelectric conversion means is provided in an interior of the first arm unit.

(10)

The medical observation apparatus according to any one of (7) to (9), further including a transmission means provided in an interior of the support unit and configured to transmit an imaging signal outputted by the microscope unit, wherein the transmission means further includes an optical fiber configured to transmit an optical signal converted by the photoelectric conversion means.

(11)

The medical observation apparatus according to any one of (1) to (10), further including a manipulation input unit provided on a side surface of the microscope unit and configured to accept a manipulation input to the medical observation apparatus.

(12)

A medical observation system including:

the medical observation apparatus according to any one of (1) to (11);

a control device configured to perform signal processing on the imaging signal outputted by the microscope unit to create image data for display; and a display device configured to display an image corresponding to image data created by the control device.

(13)

A medical observation apparatus including:

a columnar microscope unit configured to image a minute part of an object to be observed with magnification;

a support unit including a first joint unit connected to the microscope unit and supporting the microscope unit movably; and a photoelectric conversion means provided in an interior of a portion of the support unit on a root end side with respect to the first joint unit and configured to convert an imaging signal outputted by the microscope unit to an optical signal and output the converted signal.

REFERENCE SIGNS LIST 1 medical observation system
2, 2A, 2B, 2C, 9 medical observation apparatus
3 control device
4 display device
5 base unit
6 support unit
7, 501 microscope unit
11 first joint unit
12 second joint unit
13 third joint unit
14 fourth joint unit
15 fifth joint unit
16 sixth joint unit
21 first arm unit
22 second arm unit
23 third arm unit
24 fourth arm unit
25 fifth arm unit
71 cylindrical unit
72 imaging unit
73 arm manipulation switch
74 cross lever
75 upper cover
76, 212 axis unit
76a, 211b, 212a, 752a hollow portion
81 cable group
82, 83, 88, 89 bundling unit
84 FPGA board
85 flexible board
86 photoelectric composite module
87 composite cable
111, 211, 221 outer shell
111a, 211a through hole
112, 121, 122 axially supporting unit
113, 123 holding unit
502 eyepiece
601 imaging unit
602 monitor
721 optical system
722, 723 imaging element
751 circular cylindrical portion
752 hollow discoidal portion

The invention claimed is:

1. A medical observation apparatus comprising:
a camera configured to image an object and output an imaging signal;
a support configured to hold the camera; and
a photoelectric converter provided in an interior of the support and configured to convert the imaging signal outputted by the camera to an optical signal and output the converted optical signal.

2. The medical observation apparatus according to claim 1, further comprising:
a transmission path provided in the interior of the support and configured to transmit the imaging signal outputted by the camera.

3. The medical observation apparatus according to claim 2, wherein the transmission path includes a plurality of thin coaxial cables passing through an interior of a first joint of the support and configured to transmit the imaging signal outputted by the camera.

4. The medical observation apparatus according to claim 3, wherein part of the plurality of thin coaxial cables extend so as to form a bundle passing through an axis in a height direction of the camera in the interior of the first joint.

5. The medical observation apparatus according to claim 4, further comprising:
two bundling devices individually bundling both end portions of a portion of the plurality of thin coaxial cables where the plurality of thin coaxial cables extend so as to form the bundle.

6. The medical observation apparatus according to claim 1, further comprising:
a transmission path provided in the interior of the support and configured to transmit the imaging signal outputted by the camera,
wherein the transmission path includes a plurality of thin coaxial cables passing through an interior of a first joint in the support, each of the plurality of thin coaxial cables having one end connected to the camera and another end connected to the photoelectric converter, and configured to transmit the imaging signal outputted by the camera to the photoelectric converter.

7. The medical observation apparatus according to claim 1, wherein the photoelectric converter is provided in an interior of a first arm of the support.

8. The medical observation apparatus according to claim 1, further comprising:
a transmission path provided in the interior of the support and configured to transmit the imaging signal outputted by the camera,
wherein the transmission path further includes an optical fiber configured to transmit the optical signal converted by the photoelectric converter.

9. The medical observation apparatus according to claim 1, further comprising:
a manipulation switch provided on a side surface of the camera and configured to accept a manipulation input to the medical observation apparatus.

10. The medical observation apparatus according to claim 1, wherein the support includes a first joint configured to hold the camera in a rotationally movable manner around a first axis parallel to a height direction of the camera.

11. The medical observation apparatus according to claim 10, wherein the support includes a first arm configured to hold the first joint and extending in a direction different from the height direction of the camera.

12. The medical observation apparatus according to claim 11, wherein the support includes a second joint configured to hold the first arm in a rotationally movable manner around a second axis orthogonal to the first axis.

13. The medical observation apparatus according to claim 12, wherein the support includes a second arm configured to hold the second joint.

14. The medical observation apparatus according to claim 13, wherein the first and second axes define a plane which includes a circle which contains a cross section of the camera, a cross section of the first joint and the second joint, a cross section of the first arm and the second arm, and a center at a focus position of the camera and passes through an end point of the first joint that is at a maximum distance from the focus position.

15. The medical observation apparatus according to claim 14, wherein the second axis passes through a side that is nearer to the first joint than a center in a height direction of a columnar portion composed of the camera and the first joint.

16. The medical observation apparatus according to claim 1, wherein
the camera is a columnar microscope.

17. A medical observation system comprising:
a medical observation apparatus including
a camera configured to image an object and output an imaging signal, and
a support
configured to hold the camera, and
a photoelectric converter provided in an interior of the support and configured to convert the imaging signal outputted by the camera to an optical signal and output the converted optical signal;
control circuitry configured to perform signal processing on the imaging signal outputted by the camera to create image data for display; and
a display device configured to display an image corresponding to image data created by the control circuitry.

18. The medical observation system according to claim 17, wherein the support includes
a first joint configured to hold the camera in a rotationally movable manner around a first axis parallel to a height direction of the microscope,
a first arm configured to hold the first joint and extending in a direction different from the height direction of the microscope,
a second joint configured to hold the first arm in a rotationally manner around a second axis orthogonal to the first axis, and
a second arm configured to hold the second joint.

19. The medical observation system according to claim 18, wherein the first and second axes define a plane which includes a circle which contains a cross section of the camera, a cross section of the first joint and the second joint, a cross section of the first arm and the second arm, and a center at a focus position of the camera and passes through an end point of the first joint that is at a maximum distance from the focus position.

* * * * *